United States Patent [19]

Civin

[11] Patent Number: 5,081,030
[45] Date of Patent: Jan. 14, 1992

[54] RELEASE OF CELLS FROM AFFINITY MATRICES

[75] Inventor: Curt I. Civin, Baltimore, Md.

[73] Assignee: The Johns Hopkins University, Baltimore, Md.

[21] Appl. No.: 342,938

[22] Filed: Apr. 25, 1989

[51] Int. Cl.$^5$ .................... C12N 5/08; A61K 35/28
[52] U.S. Cl. ........................ 435/240.2; 435/240.23; 435/2; 435/267; 424/577
[58] Field of Search .......... 435/240.2, 240.23, 240.243

[56] References Cited

U.S. PATENT DOCUMENTS 4,714,680 12/1987 Civin .
4,814,433 3/1989 Fredrickson .

OTHER PUBLICATIONS

Perlman, et al., Methods in Enzymology, vol. 19, Proteolytic Enzymes pp. 249-250, 1970.
Worthington Enzyme Manual pp. 136-137, 1972.
Berenson et al., "Positive Selection of Viable Cell Populations Using Avidinbiotin Immunoadsorption", J. Immunol. Meth. (1986), 91:11-19.
Berenson et al., "Antigen CD34+Marrow Cells Engraft Lethally Irradiated Baboons", J. Clin. Invest. (1988) 81:951-955.
Gaudernack et al., "Isolation of Pure Functionally Active CD8+T-Cells", J. Immunol. Meth. (1986) 90:179-187.
Gee et al., "Purging Tumor Cells from Bone Marrow by the Use of Antibody and Complement: A Critical Appraisal", J. Natl. Can. Inst. (1988), 80:154-159.
Kannourakis et al., "Fractionation of Normal and B--thalassemic Human Hemopoietic Progenitor Cells by Immunomagnetic Beads," Exp. Hematol. (1987), 15:1103-1108.
Lea et al., "Magnetic Monosized Polymer Particles for Fast and Specific Fractionation of Human Mononuclear Cells," Scan. J. Immunol. (1985), 22:207-216.
Mage et al., "Mouse Lymphocytes with and without Surface Immunoglobulin:Preparative Scale Separation in Polystyrene Tissue Culture Dishes Coated with Specifically Purified Anti-Immunoglobulin," J. Immunol. Meth. (1977), 15:47-56.
Muller-Sieburg et al., "Isolation of Two Early B Lymphocyte Progenitors from Mouse Marrow: A Committed Pre-Pre-B Cell and a Clonogenic Thy-1$^{10}$ Hemato-Stem Cell," (1986), 44:653-662.
Schlossman et al., "Specific Purification of Lymphocyte Populations on a Digestible Immunoabsorbent," J. Immunol. (1973) 110:313-315.
Schrempf-Decker et al., "Helix Pomatia Agglutinin (HpA) Affinity Chromatography: The Isolation of Pure B-and T-Cell Populations and Their Use for the Routine HLA-DR (Ia) Serology," J. Immunol. Meth. (1980), 32:285-296.

Wigzell et al., "Cell Separation on Antigen-Coated Columns," J. Exp. Med. (1969), pp. 23-36.
Wysocki et al., "'Panning' for Lymphocytes: A Method for Cell Selection," Proc. Natl. Acad. Sci. U.S.A. (1978), 75:2844-2848.
Yeager et al., "Autologous Bone Marrow Transplantation in Patients with Acute Nonlymphocyte Leukemia, Using Ex Vivo Marrow Treatment with 4-Hydroperoxy-cyclophosphamide," New England J. Med. (1986), 315:141-147.
Anderson et al., "Isolation and Characterization of Human B. Lymphocyte Enriched Populations," J. Immunol Meth. (1983), 61:283-292.
Bast et al., "Elimination of Malignant Clonogenic Cells from Human Bone Marrow Using Multiple Monoclonal Antibodies and Complement," Can. Res. (1985), 45:499-503.
Egeland et al., "A Rapid Rosette Technique for Quantitation and Separation of Mononuclear Cell Subsets Using Monoclonal Antibodies," J. Immunol. Meth. (1982), 55:213-219.
Berenson et al., "Elimination of Daudi Lymphoblasts from Human Bone Marrow Using Avidin-Biotin Immunoadsorption," Blood (1986), 67:509-515.
Berenson et al., "Cellular Immunoabsorption Using Monoclonal Antibodies," Transplantation (1984), 38:136-143.
Emerson et al., "Purification of Fetal Hematopoietic Progenitors and Demonstration of Recombinant Multipotential Colony-stimulating Activity," J. J. Clin. Invest. (1985), 76:1286-1290.

(List continued on next page.)

Primary Examiner—Elizabeth C. Weimar
Assistant Examiner—George C. Elliott
Attorney, Agent, or Firm—Banner, Birch, McKie & Beckett

[57] ABSTRACT

The present invention comprises a process for release from the cell-receptor complex of positively selected cells in viable, functional condition, where a ligand involved in the particular receptor-ligand interaction utilized for the affinity purification is selectively attacked by one or more degradative enzymes specific for that ligand. A resulting cell suspension can be obtained substantially free of receptor material.

This invention, in one embodiment, contemplates a method for positive stem cell selection, utilizing anti-MY10 and immunomagnetic microspheres to isolate CD34-positive marrow cells and employing an enzyme to release micropheres from the isolated CD34-positive cells. Reproducible enzymatic cleaving of immunomagnetic microspheres from MY10-positive cells can be achieved by brief treatment of the preparation with papain or chymopapain. The isolated CD34-positive cells are particularly desirable for bone marrow transplantation.

5 Claims, No Drawings

OTHER PUBLICATIONS

Berenson et al., "Engraftment of Dogs with Ia-Positive Marrow Cells Isolated by Avidin-Biotin Immunoadsorption," Blood (1987), 69:1363–1367.

Berenson et al., "Avidin-Biotin Immunoadsorption: A Technique to Purify Cells and Its Potential Applications," Progress in Bone Marrow Transplantation (1987), pp. 423–428.

Ghetie et al., "Separation of Cells by Affinity Chromatography on SpA-Sepharose 6MB," J. Immunol. Meth. (1978), 21:133–141.

Kretser et al., "The Separation of Cell Populations Using Monoclonal Antibodies Attached to Sepharose," Tissue Antigens (1980), 16:317–325.

Kemshead et al., "Monoclonal Antibodies and Magnetic Microspheres Used for the Depletion of Malignant Cells from Bone Marrow," Advances in Neuroblastoma Research (1985) pp. 413–423.

Rembaum et al., "Cell Labeling and Separation by Means of Monodisperse Magnetic and Nonmagnetic Microspheres," in Davis et al., Micospheres and Drug Therapy, Elsevier, Amsterdam (1984), pp. 383–391.

Civin et al., "Antigenic Analysis of Hematopoiesis," J. Immunol. (1984) 133:157–165.

Strauss et al., "Antigenic Analysis of Hematopoiesis v. Characterization of My-10 Antigen Expression by Normal Lymphohematopoietic Progenitor Cells," Exp. Hematol. (1986), 14:878–886.

Civin et al., "Antigenic Analysis of Hematopoiesis," Exp. Hematol. (1987), 15:10–17.

Engleman et al., "Studies of a Human T-Lymphocyte Antigen Recognized by a Monoclonal Antibody," Proc. Natl. Acad. Sci. U.S.A. (1981), 78:1791–1795.

Basch et al., "Cell Separation Using Positive Immunoselective Techniques," J. Immunol. Meth. (1983), 56:269–280.

Griffin et al., "Induction of Proliferation of Purified Human Myeloid Progenitor Cells . . . ", Blood (1984) 63(4):904–911.

Watt et al., "Distribution and Epitope Analysis of the Cell Membrane Glycoprotein (HPCA-1) Associated with Human Hemopoietic Progenitor Cells", Leukemia, vol. 1, No. 5, May 1987, pp. 417–426.

Thomas et al., "Specific Binding and Release of Cells From Beads Using Cleavable Tetrameric Antibody Complexes", J. Immunol. Meth., 120:221–231.

Nakajima et al., "Relationship Between Human IgE-Binding Factors (IgE-BF) and Lymphocyte Receptors for IgE", J. Immunol., 139:848–854.

RELEASE OF CELLS FROM AFFINITY MATRICES

The U.S. Government has a paid up license in this invention and the right in limited circumstance to require the patent owner to license others on reasonable terms as provided for by the terms of Grant No. R01 CA 32318 awarded by the National Institutes of Health.

FIELD OF THE INVENTION

The invention is directed toward a method of releasing viable cells from cell-receptor affinity complexes.

BACKGROUND OF THE INVENTION

Bone marrow transplantation (BMT) is now an important treatment modality for aplastic anemia and leukemia, and BMT strategies are under intense investigation for utility in other malignancies and in genetic disease. Two forms of bone marrow transplantation have been developed, namely, the allogeneic (from a genetically different donor) and autologous (using marrow cryopreserved prior to ablative therapy) forms. Both are based on a principle of high dose chemotherapy and/or radiation therapy followed by repopulation of the marrow by infusion.

Due to the inability to transfer only the stem cell population, the applicability of allogeneic BMT remains restricted by graft vs. host disease (GVHD), which is apparently mediated by T lymphocytes in the graft cell population. Risk of GVHD has limited allogeneic BMT to use only in highly fatal diseases, and even then, only for patients with HLA-matched donors, usually siblings. Autologous BMT can avoid most of the problems associated with allogeneic transplants. In autologous BMT, however, it is necessary to reintroduce only desirable cell populations free of diseased cell populations (e.g., occult tumor cells) to avoid re-introduction of the disease.

The problems associated with both allogeneic and autologous BMT can be alleviated by using purified stem cell populations for the graft. These purified populations can be obtained from marrow cell suspensions by positive selection (collecting only the desired cells) or negative selection (removing the undesirable cells), and the technology for capturing specific cells on affinity materials is well developed. (Wigzel, et al. (1969), *J. Exp. Med.*, 129:23; Schlossman, et al. (1973), *J. Immunol.*, 110:313; Mage, et al. (1977), *J. Immunol. Meth.*, 15:47; Wysocki, et al. (1978), *Proc. Nat. Acad. Sci.*, 75:2844; Schrempf-Decker, et al. (1980), *J. Immunol. Meth.*, 32:285; Muller-Sieburg, et al. (1986), *Cell*, 44:653.)

Monoclonal antibodies against antigens peculiar to mature, differentiated cells have been used in a variety of "negative" selection strategies to remove undesired cells (i.e., to deplete T cells or malignant cells from allogeneic or autologous marrow grafts, respectively). (Gee, et al., *J.N.C.I.* (1988) 80:154-9; Gee, al., "Proc. of 1st Int. Workshop on Bone Marrow Purging," in *Bone Marrow Transpl.*, Supp. 2, London, MacMillan, 1987.) Successful purification of human hematopoietic cells by negative selection with monoclonal antibodies and immunomagnetic microspheres has been reported which involved use of multiple monoclonal antibodies, thus making it more costly for clinical application than positive selection. (Griffin, et al., *Blood*, 63:904 (1984); Kannourakis, et al., *Exp. Hematology*, 15:1103-1108 (1987).)

Most studies report 1 to 2 orders of magnitude reduction in the target cell level following monoclonal antibody treatment. This may not be adequate T lymphocyte depletion necessary to prevent GVHD in allogeneic transplants, and it is certainly insufficient in autologous bone marrow transplantation where $10^6$ to $10^9$ malignant cells may be present in the patient's marrow.

Positive selection of normal marrow stem cells is an alternative for treatment of the marrow graft. The procedure employs a monoclonal antibody which selectively recognizes human lymphohematopoietic progenitor cells, such as the anti-MY10 monoclonal antibody that recognizes an epitope on the CD34 glycoprotein antigen. Cells expressing the CD34 antigen include essentially all unipotent and multipotent human hematopoietic colony-forming cells (including the pre-colony forming units (pre-CFU) and the colony forming unit-blasts (CFU-Blast)) as well as the very earliest stage of committed B lymphoid cells, but NOT mature B cells, T cells, NK cells, monocytes, granulocytes, platelets, or erythrocytes. See Civin, U.S. Pat. No. 4,714,680.

CFU yields in MY10-positive cell populations are far higher than the 0.1-23% range of recovery of CFU observed after treatment of marrow grafts with 4-hydroperoxycyclophosphamide, a cyclophosphamide metabolite that "purges" malignant cells from marrow grafts without ablating the ability of the marrow to engraft. (Yeager, et al. (1986), *N. Eng. J. Med.*, 315:141.) Positive selection utilizing CD34 monoclonal antibody also appears more feasible (over the long term) for BMT than negative selection strategies for isolations of rare progenitor cells from marrow or blood, offering advantages such as specificity, simplicity, and cost in treatment of diseases other than leukemia.

Recently, Berenson, et al. (1986), *J. Immunol. Meth.*, 91:11-19, disclosed a method for large scale positive selection of class II antigen-positive or CD34-positive cells from marrow, using monoclonal antibody columns. The preliminary results were based on in vitro CFU assays on separated human marrow samples, and actual in vivo BMT experiments in primates. (Berenson, et al. (1988), *J. Clin. Invest.*, 81:951-960.) The primate experiments were possible, since some epitopes of the MY10 glycoprotein are shared between humans and primates.

Marrow cells tend to aggregate nonspecifically at the high cell density that results from slow percolation of marrow through the column necessitated by the relatively low avidity of monoclonal antibody for cell surface antigen, so this work took advantage of the high affinity avidin-biotin interaction. Marrow cells were first labelled with monoclonal antibody, then with biotin-labelled anti-mouse Ig. Upon percolation through a column of avidin-coated macroscopic agarose beads, antigen-positive cells bound to the column, even at high flow rates. After washing of the column to remove unbound cells, bound cells were physically sheared from the beads by vigorous pipetting of the column contents. This release method does not guarantee that all cell-antibody complexes (i.e., antibody-coated cells) were eliminated from the final cell suspension.

Further refinement of techniques for positive selection of MY10-positive cells are available which do not require treatment of marrow cells with multiple reagents (CD34 monoclonal antibody, biotinylated polyclonal anti-mouse antibody, avidin-conjugated macrobeads). Magnetic microspheres with low nonspecific avidity for cells are commercially available, either in uncoated form (for adsorption of the desired antibody) or coated with anti-mouse Ig. Cell trapping can more readily be avoided with monodisperse microspheres, and the immunomagnetic microsphere technique has been shown to be effective for positive selection in, e.g., Gaudernack, et al., *J. Immunol. Meth.*, 90:179 (1986).

The most desirable cell suspension for BMT would be one that is substantially free of cell:receptor complexes. Thus, the problem of how to release positively selected cells from the affinity matrix once they have been separated from the non-selected cells still remains.

SUMMARY OF THE INVENTION

It is an object of this invention to provide a method for release of cells bound to affinity matrices which preserves the viability and function of the cells.

It is also an object of this invention to provide a method for release of positively selected cells from the receptors used in selecting them, so that the cells remain in viable, functional condition.

It is a further object of this invention to provide a method for the recovery of viable, functional bone marrow cells characterized by the CD34 surface antigen which are substantially free of all foreign protein, particularly antibodies to the CD34 antigen.

These and other objects may be achieved by the practice of the invention disclosed herein.

The present invention comprises a process to release positively selected cells in viable, functional condition, where a ligand involved in the particular receptor-ligand interaction utilized for the affinity purification is selectively attacked by one or more degradative enzymes specific for that ligand.

The exact type of selective attack can be controlled by the enzyme selection to be non-toxic and non-injurious to the cells in question and directed to a limited number of cell surface structures. By attacking the cell surface "ligand," rather than the receptor on the affinity matrix, the cells are freed of the "foreign material" which had coated their surfaces, at the cost of only a minor nick in certain exposed membrane molecules. The resulting cell suspension is substantially free of receptor material. For some in vitro processes and procedures receptor-carrying cells may be suitable, but for in vivo processes and particularly for therapeutic purposes, these receptors can be extremely detrimental.

This invention, in one embodiment, contemplates a method for positive "stem cell" selection, utilizing anti-MY10 and immunomagnetic microspheres to isolate CD34-positive marrow cells and employing an enzyme to release microspheres from the isolated CD34-positive cells. Reproducible enzymatic cleaving of immunomagnetic microspheres from MY10-positive cells can be achieved by brief treatment of the preparation with papain or chymopapain. The chymopapain treatment does not produce detectable damage to human colony-forming cells or rat stem cells. When employing CD34-positive monoclonal-antibody-coated microspheres, this immunomagnetic microsphere technique has fewer steps than the avidin-biotin system.

DETAILED DESCRIPTION OF THE INVENTION

This invention contemplates release of cells from receptors bound specifically to their surfaces. The cells contemplated by this invention comprise animal cells, preferably mammalian cells, where the cells are characterized by the presence, on their surface, of surface ligands—molecules which comprise one or more binding sites for particular receptors. These ligands are peculiar to the cell-type contemplated by this invention and absent on other cell-types which are undesirable for a particular purpose. This purpose is optimally therapeutic, involving administration of a selected subpopulation of cells to a patient. Suitable cell types include stem cells from blood or bone marrow, hormone-secreting cells, particular types of lymphocytes, and LAK cells, as well as other cell types that will be apparent to those of ordinary skill in the art. Selection of the subpopulation comprises binding of the peculiar surface ligands by receptors.

Specific cell surface ligands to which the receptors bind are carbohydrates, proteins, lipids, and combination molecules, including, but not limited to, well-known cell surface antigens, cell membrane proteins and the carbohydrate portion of cell surface glycolipids and glycoproteins. The receptors contemplated by this invention include, without limitation, antibodies specific for cell surface antigens, lectins specific for the carbohydrate portions of cell-surface glycolipids and glycoproteins and other proteins that bind to cell surface ligands. The receptors may be in their native state, they may be bound in turn to other binding moieties, or they may be covalently attached to another component, such as a fluorescent label or an insoluble support matrix. Materials that may be used for insoluble support matrices are well known in the art and include protein, carbohydrates, polystyrene, polyacrylamide, magnetic material, and other materials. A variety of support configurations are known in the art including flat surfaces, beads, microspheres and the like.

Cell-receptor complexes are well-known in the art and are broadly contemplated for the practice of this invention. They are prepared by incubating the cells with the receptor in any medium that is suitable for maintaining cell viability, and which does not interfere with cell-receptor binding, for sufficient time to permit binding. These cell-receptor complexes are separated from other cells, which do not bind to the receptor molecules, by use of separation techniques based on properties of either the receptor molecule or the cell-receptor complex. Examples of the separation techniques include fluorescence-activated cell sorting or flow cytometry where the receptor is a fluorescent-labelled antibody, an avidin-affinity column where the receptor is a biotin-labelled antibody, and magnetic separation where the receptor is a murine antibody which reacts with the anti-mouse IgG on immunomagnetic microspheres. Separation of the cell-receptor complex is within the contemplation of this invention irrespective of the selection technique employed to obtain the complex.

After the cell-receptor complex is separated, the cells are released from the complex by treatment with a degradative enzyme, where the enzyme specifically degrades the cell surface ligand to which the receptor is bound without substantially decreasing the viability or function of the cell population. The enzyme is selected from the group consisting of carbohydrases, proteases and lipases, and is usually selected based on the known chemistry of the cell surface ligand. Proteases may be used for cell surface proteins and glycoprotein antigens, and specific carbohydrases may be used for cell surface glycolipids and glycoproteins. Examples include a neuraminidase for sialic-acid-containing surface carbohydrates, glycosidases such as N-glycanase, O-glycanase, endo-glycosidase F, endo-glycosidase H and proteases such as pepsin, papain, chymopapain, chymotrypsin and others and phospholipases C and D. Alternatively, enzymes that are recognized empirically to degrade the ligand of interest or enzymes that have been empirically determined to release the receptor from cell:receptor complexes can be used.

Effectiveness of the chosen enzyme can readily be confirmed by the following procedure. First, a cell population containing the cells of interest is incubated with the chosen enzyme (or a panel of candidate enzymes) under conditions that facilitate the activity of the enzyme(s) without compromising viability of the cells. After incubation, the cells are washed to remove the enzyme and tested for ability to bind the receptor. The cells which have been treated with the chosen enzyme are also tested for viability. If the enzyme treatment has destroyed receptor binding without reducing viability, then the enzyme is a suitable candidate.

The suitability of the enzyme for the method of this invention can be confirmed by incubation of the cells with the receptor followed by treatment with the enzyme. Then the cells are washed to remove the enzyme and the receptor, and the cells are tested for viability. If the cells are released from the receptor and remain viable, then the suitability of the enzyme choice is confirmed. Those of ordinary skill in the art can routinely apply this procedure to select appropriate enzymes for release of cells from the many well-known and characterized cell-receptor complexes.

In the practice of this invention, cell-receptor complexes, substantially free of unbound cells, are incubated with the selected enzyme in a medium suitable for suspension of the particular cell type, under gentle conditions of temperature and agitation selected to maximize viability of the cells. These conditions will be apparent to one of ordinary skill from the conditions used in isolation of the cells and in preparation of the cell:receptor complex. The incubation is continued for a period of time sufficient for substantial release of all receptors from the cell surface. The enzyme dose can be selected based on the results of routine tests concerning degradation of the cell-surface ligand. Increasing enzyme dose or increasing temperature permits reduction in the time of incubation. Time, temperature and enzyme dose for the incubation can be optimized to maximize viability of the released cells. This optimization is a routine procedure within the ordinary skill in the art.

After the enzyme treatment, cells are washed to remove the enzyme and the receptor, and the cell population is recovered in a suitable suspending medium. The washing procedures used to recover the original cell population prior to receptor binding and separation are suitable for this step. The cell population, after enzyme treatment and washing, is made up of the positively selected cell-type and substantially free of foreign, antigenic material. It is therefore particularly suited for therapeutic use.

In a particular embodiment of this invention, cells bearing the CD34 antigen are positively selected to provide a population of cells for bone marrow transplant without any foreign receptor on their surfaces. This cell population contains the lymphohematopoetic progenitor cell types but does not contain mature cells such as mature B cells, T cells, NK cells, monocytes, granulocytes, platelets and erythrocytes, nor does it contain malignant cells. The method of this invention first requires that a population of CD34-positive, receptor-bound cells be obtained based on their ability to bind anti-MY10 antibody. Procedures to prepare such populations bound to the anti-MY10 antibody are taught in U.S. Pat. No. 4,714,680 and are incorporated herein by reference. A preferred method of obtaining such a cell population comprises attaching the cells to immunomagnetic microspheres using an anti-MY10 monoclonal antibody and holding the microsphere-bound cells in place with a magnetic field while the unbound cells are washed away.

In a representative procedure, buffy coat cells are obtained from bone marrow using standard techniques, with or without Ficoll purification, and suspended at from $5 \times 10^6$ to $10^8$ cells/ml in a suitable tissue culture medium, such as Gibco TC199, preferably with 0.25% human serum albumin (HSA) present. Anti-MY10 monoclonal antibody is added at an amount in excess of the amount needed for labelling cells with the antibody, determined in separate experiments. The preferred antibody will form complexes with epitopes identified by the monoclonal antibody produced by hydridoma cell line ATCC HB-8483, identified in U.S. Pat. No. 4,714,680. The cells are incubated with the antibody for from 10 to 120 minutes (preferably from 20 to 30 minutes) at a temperature of from 0° to 40° C. (preferably about 4° C.) with gentle agitation. After incubation, the cells are washed one or more times by centrifugation using the same tissue culture medium. Then the antibody-treated cells are mixed with IgG-coated magnetic microspheres, where the IgG is specific for the species-type Ig of the anti-MY10 monoclonal antibody used to coat the cells, usually using 0.5-4 microspheres per cell. Incubation conditions are the same as those given for the incubation with anti-MY10. After the incubation, the microspheres and the microsphere-bound cells are held in the incubation vessel by a strong magnetic field and washed to remove the unbound cells. A suitable washing protocol would be three times with 10 volumes of tissue culture medium.

An alternative, less preferred method for obtaining the desired population of cells bound to magnetic microspheres involves preparing magnetic microspheres coated with the monoclonal anti-MY10 antibody and incubating the original marrow isolate directly with these microspheres under the incubation conditions given above. This alternative process involves fewer processing steps, but it may yield lower recoveries of colony-forming cells.

The desired cells are detached from the magnetic microspheres by treatment with an enzyme, preferably chymopapain. Any suitable preparation of chymopapain may be used. Therapeutic preparations designed for use in treating lumbar disc disease are particularly suitable. The cell-bound microspheres are treated with from 50 to 500 units of chymopapain per $10^7$ cells. (1 unit hydrolyzes 1 picomole of p-nitroaniline from benzoylarginine-p-nitro-anilide per second.) The treatment is performed in a suitable tissue culture medium, preferably TC199, for from 5 to 240 minutes, preferably 5 to 45 minutes, at from 4° to 40° C., preferably 30°-37° C., at a cell concentration of from $5 \times 10^6$ to $10^8$ per ml. After the incubation, the magnetic microspheres may be separated based on density or trapped by a magnetic field and the cells decanted. Preferably, the cell population is then freed of residual enzyme by centrifugal washing with tissue culture medium. The resultant cell population is particularly useful for bone marrow transplants.

The cell population of this invention can be used in therapeutic methods, such as stem cell transplantation, as well as other therapeutic methods that are readily apparent to those of skill in the art. For example, such cell populations can be administered directly by I.V. to a mammalian patient requiring a bone marrow transplant in an amount sufficient to reconstitute the patient's hematopoietic and immune system. Precise, effective quantities can be readily determined by those skilled in the art and will depend, of course, upon the exact condition being treated by the therapy. In many applications, however, an amount containing approximately the same number of stem cells found in one-half to one liter of aspirated marrow should be adequate.

The following examples are provided to illustrate specific embodiments of the present invention. The examples are included for illustrative purposes only and are not intended to limit the scope of the present invention.

EXAMPLE 1

Effects of Proteolytic Enzyme Treatment On Antigen Expression of KG1a Cells

In order to determine whether chymopapain cleaved epitopes from cells, the effect of chymopapain was tested on the KG1a human leukemia cell line. KG1a cells, coated with anti-MY10 monoclonal antibody and also uncoated, were treated with chymopapain (200 units/ml TC199, 37° C., 10 minutes), washed, and then stained with monoclonal antibodies. Chymopapain treatment resulted in the almost complete removal of anti-MY10 antibody and the MY10 epitope from KG1a cells. Other cell surface antigens, the transferrin receptor and CD45R epitopes, treated as controls, were still detectable, through decreased, on the KG1a cells.

EXAMPLE 2

Effects of Proteolytic Enzyme Treatments On Colony-Forming Capacity of Cells from Bone Marrow Effective chymopapain treatment did not appear toxic to human hematopoietic colony-forming cells. Buffy coat preparations of marrow mononuclear cells (MMC) were washed with TC199 (without additives), then treated with 200 units/ml chymopapain (or control medium) for 10–30 minutes at 37° C. ($10^7$ nucleated cells/ml TC199). Neither the initial viable cell counts nor the colony-forming capacities of the chymopapain-treated marrow cells were significantly different from those of controls (Table 1).

TABLE 1

Effect of Chymopapain Treatment on Colony Forming Capacity of MMC
$10^7$ buffy coat marrow cells were incubated for 10 or 30 minutes in 1 ml TC199 culture medium containing 200 units/ml chymopapain, pelleted, then resuspended in an identical volume for colony-forming assays.

| Duration of | Colonies per $10^5$ Cell Plated | |
|---|---|---|
| Chymopapain Treatment (min) | CFC-GM | BFU-E |
| None | 131 | 105 |
| 10 | 114 | 114 |
| 30 | 109 | 109 |

In contrast, when MMC were treated with papain (conditions: 0.026 mg/ml papain, incubation for 90 minutes), 10% of the initial functional colony-forming cells were recovered. Trypsin was found to be toxic to hematopoietic colony-forming cells.

EXAMPLE 3

Binding of Cells to Immunomagnetic Microspheres Via Anti-MY10 Monoclonal Antibody The "indirect" method of incubating cells first with anti-MY10, then with sheep anti-mouse $IgG_1$-coated magnetic microspheres, was utilized in the current experiment. $10^6$ KG1a cells or MMC ($10^7$/ml in TC199 tissue culture medium containing 1% human serum albumin [HSA] and 20 mg/1 gentamycin) were incubated at 4° C. for 30 minutes, on a hemocytology rocker-rotator mixer, with undiluted MY10 hybridoma supernatant (an amount previously determined to provide a condition of antibody excess for labelling). The cells were then washed twice by centrifugation (250×g, 10 min) with ice-cold TC199 containing gentamycin and 0.25% HSA.

The monoclonal antibody-treated KG1a cells or MMC (in 1 ml TC199 containing gentamycin and 1% HSA) were mixed with anti-mouse $IgG_1$-coated (Dynabeads M-450 from Dynal Corp.) magnetic microspheres in a screw-top tube, usually at a ratio of 0.5–4 microspheres per KG1a cell or per MMC. The microsphere-cell mixtures were vortexed gently and incubated at 4° C. for 30 minutes, on a hematology rocker-rotator mixer. After incubation, the cells were separated, using a strong magnet to hold the microspheres and microphere-bound cells to the wall of the tube while unbound cells were poured from the tube. The microsphere/cell complexes were washed in this fashion 3 times with 10 ml TC199 without additives. The MY10-positive and MY10-negative marrow cell fractions were examined, using a phase contrast microscope, for the presence of rosettes and free cells, and saved for analyses as described below.

Using Ficoll-Hypaque purified low density MMC cells, a microsphere per MMC ratio of 0.5:1 was found to deplete 90% of the hematopoietic colony-forming cells from the CD34-negative cell fraction.

EXAMPLE 4

Release of Microspheres From KG1a Cells Using Proteolytic Enzymes

A series of experiments was performed, attempting to detach immunospheres from KG1a cells, using papain treatment for 1–3 hours over a wide range of papain concentrations. Treatment under these conditions with papain (concentration 0.026 mg/ml) resulted in essentially 100% release of microspheres from KG1a cells with 84–93% viable cell recovery. In contrast, dyspase (Boehringer Mannheim) was not effective at releasing immunomagnetic microspheres linked to KG1a cells by anti-MY10. Trypsin was not tested for efficacy at releasing microspheres from KG1a cells because of its toxicity to bone marrow colony-forming cells.

As an alternative to papain, MY10/microsphere/cell complexes were treated with chymopapain (Chymodiactin ®, Flint Laboratories/Boots Co. [U.S.A], Lincolnshire, ILL.). These experiments showed chymopapain to be effective at releasing immunomagnetic microspheres from KG1a cells over a wide range of concentrations and times of incubation. In five experiments, treatment of KG1a cells (bound via anti-MY10 to immunomagnetic microspheres) using 200 units/ml chymopapain for 10 minutes at 37° C. resulted in 90–109% (mean=100%) recovery of viable KG1a cells; treatment for 45 minutes was only marginally more toxic.

EXAMPLE 5

Isolation of MY10-Positive Cells From Marrow

MY10-positive cells were isolated using anti-MY10 and immunomagnetic microspheres according to Example 3 (0.5 microspheres per nucleated cell), and separation of MY10-positive cells from microspheres with chympapapin according to Example 4 (200 units/ml, 37° C., 10 minutes). The resulting cell population was usually 50 to 90% blasts compared to 1 to 3% blasts in the starting cell preparation. The main contaminating cell-type was nucleated erythrocytes. Lymphoctyes and granulocytes were usually present in small numbers. MY10-positive marrow cells have been previously shown to have blast and early lymphoid morphology.

EXAMPLE 6

Light Scattering Characteristics of Isolated MY10-positive Marrow Cells

On flow cytometry CD34-positive, lymphohematopoietic cells have light scattering properties characteristic of the "BLAST" and "LYMPH" windows. Consistent with this, the immunomagnetic microsphere enriched MY10-positive cell population of Example 5 contained predominantly cells with "BLAST" and "LYMPH" light scattering properties. The percentage of cells which was included in the "BLAST" window was particularly informative, since fewer than 10% of unseparated bone marrow cells show this type of light scatter, while the MY10-positive cell fraction usually had 60–70% of cells in the "BLAST" window.

EXAMPLE 7

Cell Surface Antigens of Isolated MY10-positive Cells

Freshly islolated cell fractions of Example 5 were tested for expression of MY10 and other cell membrane antigens. The MY10-negative cell fractions were depleted (by approximately 90%) of cells expressing detectable MY10, as compared to unseparated marrow, indicating efficient binding of anti-MY10 coated cells by the microsphere procedure. The majority of cells in the "MY10-positive" cell fractions did not, after re-exposure to anti-MY10, bind the anti-MY10 monoclonal antibody (by indirect immunofluorescence).

Of particular importance, other epitopes of the CD34 glycoprotein were found to be resistant to the chymopapain treatment. Direct enumeration of the CD34-positive cells in the selected cell population was thus possible by using monoclonal antibodies directed against these chymopapain-resistant CD34 epitopes. Other cell surface antigens were found to be still detectable after the chymopapain treatment; these include HLA-DR, CD3, CD4, CD5, CD14, CD19, CD20 and CD45. The retention of the CD3, CD4 and CD5 epitopes permits monitoring of residual T cells in the MY10-positive cell fraction.

EXAMPLE 8

Hematopoietic Colony-Forming Capacity of Isolated MY10-positive Marrow Cells The MY10-positive cell fractions of Example 5, obtained using the immunomagnetic microspheres, were enriched in CFC-GM (23–41-fold) and BFU-E (21–31-fold), with 11–45% recovery of these colony-forming cells in the MY10-positive cell fraction. The MY10-negative cell fractions were correspondingly depleted of colony-forming cells.

To ensure that the isolation procedure did not diminish the colony-forming capacity of the recovered cells, the isolation procedure was run in parallel with another selection procedure (panning). The nearly identical results achieved by the two procedures (Table 2) indicate that excellent colony-forming capacity is retained by the MY10-positive cells following incubation with the microspheres and treatment with chymopapain.

TABLE 2

Comparison of Immune Adherence Progenitor Cell Purification from Normal Human Bone Marrow Cells Using Immunomagnetic Beads versus "Panning"

| | | Control Unseparated | Panning | | Microspheres | |
|---|---|---|---|---|---|---|
| | | | MY10− Cells | MY10+ Cells | MY10− Cells | MY10+ Cells |
| Exp. 1 | | | | | | |
| Viable cell recovery (%) | | 100 | 85 | 2.1 | 82 | 2.5 |
| Colonies/10⁵ cells: | CFC-GM | 159 | 43 | 3740 | 11 | 4190 |
| | BFU-E | 95 | 10 | 1610 | 0 | 1975 |
| | Mixed | 6 | 0 | 125 | 0 | 163 |
| Exp. 2 | | | | | | |
| Viable cell recovery (%) | | 100 | 96 | 1.6 | 98 | 1.4 |
| Colonies/10⁵ cells: | CFC-GM | 305 | 93 | 12000 | 43 | 10750 |
| | BFU-E | 130 | 70 | 4380 | 13 | 2880 |
| | Mixed | 0 | 0 | 625 | 2 | 375 |

EXAMPLE 9

Isolation of MY10-positive Cells From Marrow Buffy Coat

The isolation procedure was tried on a buffy coat (rather than a Ficoll-Hypaque) preparation of marrow cells. A MY10-positive cell fraction could be isolated from marrow buffy coat which was substantially enriched in cells with blast cell morphology, the light scattering characteristics of MY10-positive cells, and in hematopoietic colony-forming cells. However, it was necessary to use a ratio of 1–4 microspheres per nucleated cell to efficiently isolate the MY10-positive cells. It was therefore decided to use a Ficoll-Hypaque gradient to isolate MMC, since with Ficoll-purified cells only 0.5 microsphere per nucleated cell was necessary for the isolation procedure.

EXAMPLE 10

Chymopapain Treatment of Normal Rat Bone Marrow Cells

Rat marrow cells were treated with either chymopapain or control medium as in Example 2. The treatment had no significant effect on cell viability (trypan blue dye exclusion). In addition, no significant injury to rat colony-forming cells was detected by in vitro cultures in agar.

EXAMPLE 11

Effect of Chymopapain Treatment on Rat Stem Cells Assayed by Marrow Transplantation Table 3 shows the ability of the treated rat bone marrow cells of Example 10 to reconstitute hematopoiesis after injection into lethally irradiated, syngeneic rats, using as marrow grafts injected cell doses chosen such that the cell number would be nearly limiting for engraftment. Experiments 1 and 2 were performed using grafting cell doses of 1 and 5 million cells per rat, and Experiment 3 used 2 and 5 million cells per rat. All animals receiving no marrow cell rescue (total body irradiation only) died 12-14 days after irradiation. These animals had marked pallor prior to death, and their bone marrows were extremely hypocellular upon autopsy.

In contrast, when 5 million treated or control cells were engrafted, all animals survived. At a more limiting grafting cell dose of 2 million starting cells (based on cell counts prior to chymopapain or sham treatment), some animals died, but nearly all lived several days beyond the radiation controls; survival was identical in the treated vs. control groups. Autopsies of these animals suggested early marrow engraftment, with identifiable hematopoietic cells within a hypocellular marrow. Similar results were obtained using a dose of 1 million starting cells per irradiated rat. Extension of the time of chymopapain incubation with marrow cells from 10 to 30 minutes did not decrease the ability of treated cells to reconstitute hematopoiesis in these irradiated rats.

TABLE 3

Effect of Chymopapain Treatment on Engraftment of Rat Bone Marrow Cells in Lethally Irradiated Rats

| Treatment (Sham or Chymo) | Treatment Duration (min) | Grafting Cell Dose (millions) | Days of Survival (for individual rats) Exp. 1 | Exp. 2 | Exp. 3 | Overall Survival (n/total) |
|---|---|---|---|---|---|---|
| — | — | None | 12,12 | 13,13 | 13,14 | 0/6 |
| — | — | 1 | 60+,60+ | 50+,50+ | ND | 4/4 |
| — | — | 5 | 60+,60+ | 50+,50+ | 25+,25+ | 6/6 |
| Sham | 10 | 1 | 18,18 | 14,15 | ND | 0/4 |
| Chymopapain | 10 | 1 | 15,21 60+, 60+ | 13,13 15,21 | ND | 2/8 |
| Sham | 10 | 2 | ND | ND | 19,20 25+,25+ | 2/4 |
| Chymopapain | 10 | 2 | ND | ND | 22,25+ 25+,25+ | 3/4 |
| Sham | 10 | 5 | 60+,60+ | 50+,50+ | ND | 4/4 |
| Chymopapain | 10 | 5 | 60+,60+ | 50+,50+ | 25+,25+ 25+,25+ | 8/8 |
| Chymopapain | 30 | 1 | 15,17 17,18 | 14,15 20,20 | ND | 0/8 |
| Sham | 30 | 2 | ND | ND | 25+,25+ 25+,25+ | 4/4 |
| Chymopapain | 30 | 2 | ND | ND | 23,25+ 25+,25+ | 3/4 |
| Sham | 30 | 5 | ND | ND | 25+,25+ 25+,25+ | 4/4 |
| Chymopapain | 30 | 5 | ND | ND | 25+,25+ 25+,25+ | 4/4 |

EXAMPLE 12

Large-Scale Isolation of CD34-Positive Cells From Bone Marrow

Bone marrow was processed as described in Examples 3 and 4 except that a COBE 2991 processing unit was used for the Ficoll processing and washing steps, and incubations were carried out in tissue culture flasks of 75 cm$^2$ surface area. The amount of MY10 monoclonal antibody used, the microsphere:cell ratio and the concentration of chymopapain were the same as in the previous Examples. Manual 100-cell differentials were performed on cytospins of the isolated cells from two separate isolation runs (Table 4). The quickness of the manual differential makes it useful for rapidly assessing the purity of a cell population.

The most informative characterization of the cell types present in the final, isolated population was provided by the use of direct and indirect immunofluorescence assays for cell surface markers. Most of the monoclonal antibodies directed against cell surface markers recognize epitopes which are not damaged or destroyed by chymopapain as used in the isolation procedure. While the epitope recognized by monoclonal MY10 does not remain intact after the treatment with chymopapain, other determinants on the CD34 glycoprotein do remain intact. TUK3 monoclonal antibody reacts with one such determinant and thus allows a direct enumeration of the CD34-positive cells present in the final isolated population. A sample of the TUK3 antibody was obtained from Dr. Barbara Uchanska-Ziegler, Institute fur Experimentelle Imunologie, Universitat Marburg, Deutschhausstrasse 1, D-3550 Marburg, Germany. In Isolation 1, 95% of the cells reacted with TUK3 while in Isolation 2 only 43% were labelled.

A variety of other monoclonal antibodies are used to identify cells other than CD34-positive cells present in the final isolate. An anti-leucocyte FITC (CD45)+Anti-Leu M3 PE (CD14) reagent (LeucoGATE, Becton Dickinson Immunocytometry Systems) allows identification of nucleated RBC, mature lymphocytes, and monocytes. Anti-Leu 1 (CD5) and Anti-Leu 4(CD3) are used to identify T cells while Anti-Leu 12 (CD19) and Anti-Leu 16 (CD20) are used as B cell markers. Granulocytes are marked by a monoclonal antibody directed against CD15. The information obtained by use of these antibodies was analyzed to give the cell distribution by cell surface marker presented in Table 4.

TABLE 4

Composition of Isolated CD34-positive Cell Populations

| Cell Type | Manual Differential % | Cell Surface Markers (%) |
|---|---|---|
| Isolation 1 | | |
| Blasts | 85 | 95 |
| Nucleated RBC | 3 | 1 |
| Lymphocytes | 0 | 0.5 |
| Granulocytes | 12 | 3.5 |
| Isolation 2 | | |
| Blasts | 36 | 43 |
| Nucleated RBC | 48 | 32 |
| Lymphocytes | 7 | 18 |
| Granulocytes | 9 | 5 |

EXAMPLE 13

Light Scattering Characteristics of Isolated Bone Marrow Cells

Plots of forward vs. side scatter were obtained for the three cell populations produced in the isolations of Example 12: 1) unseparated, Ficoll-processed cells; 2) cells which did not bind to microspheres and are therefore depleted of MY10-positive cells; and 3) the cells isolated after chymopapain treatment of cell-microsphere complexes which include the MY10-positive cells. MY10-positive cells have light scattering properties characteristic of the "BLAST" and "LYMPH" windows. The third window is the "GRAN" window. The percent of each cell population occurring in each of these windows is reported in Table 5. In both Isolations 1 and 2, unseparated cells and the MY10-depleted cells have similar light scattering profiles and similar cell distributions among the three windows. The isolated cells, as expected, occur predominantly in the "LYMPH" and "BLAST" windows, with the marked increase in the percentage of cells in the "BLAST" window being particularly indicative of the enrichment for MY10-positive cells.

In Isolation 2, only approximately 43% of the cells were CD34-positive as determined by cell surface markers (see Example 12). The major contaminating cell types, nucleated red blood cells and lymphocytes, also tend to have light scatter properties characteristic of the "LYMPH" window with some spillage into the "BLAST" window. Light scatter is therefore most useful for its indication of depletion of granulocytes and monocytes and for its indication of enrichment of cells occurring in the "BLAST" window which are predominantly CD34-positive cells.

TABLE 5

Distribution of Cells by Light Scatter

| | Cell Population | | |
|---|---|---|---|
| Window | Unseparated (%) | MY10 Depleted (%) | Isolated (%) |
| Isolation 1 | | | |
| Lymphocyte | 22 | 22 | 23 |
| Blast | 9 | 8 | 62 |
| Granulocyte | 38 | 39 | 3 |
| Isolation 2 | | | |
| Lymphocyte | 23 | 20 | 27 |
| Blast | 10 | 9 | 50 |
| Granulocyte | 43 | 46 | 4 |

EXAMPLE 14

Hematopoietic Colony-Forming Capacity

The final CD34-positive cell fractions obtained in Example 12 were tested for the enrichment of colony-forming cells relative to the starting and MY10-depleted cell populations. Colony forming data are presented in Table 6.

TABLE 6

Colony-Forming Capacity of Cell Fractions

| | | Unseparated Cells | Unbound Cells (MY10−) | Isolated Cells (MY10+) |
|---|---|---|---|---|
| Isolation 1 | | | | |
| Viable cell recovery (%) | | 100 | 59 | .76 |
| Colonies/$10^5$ cells: | CFC-GM | 370 | 18 | 7200 |
| | BFU-E | 186 | 8 | 1950 |
| Day 14 Blasts | | 5.8 | 0 | 47.5 |
| Isolation 2 | | | | |
| Viable cell recovery (%) | | 100 | 80 | 2.36 |
| Colonies/$10^5$ cells: | CFC-GM | 143 | 15 | 18625 |
| | BFU-E | 75 | 2.5 | 6425 |

In both isolations the final cell fraction was highly enriched for colony-forming cells. Purified MY10 cells in this assay system typically give rise to 5,000 to 10,000 colonies per $10^5$ cells planted. Thus the functional capacity of the CD34-positive cells to form colonies does not appear to be impaired by the isolation procedure, including treatment with chymopapain. Furthermore, few colony-forming cells remained in the unbound, MY10-depleted cell fraction.

I claim:

1. A method for releasing animal cells bound to antibodies specific for the MY10 epitope which comprises treating the antibody bound animal cells with chymopapain and separating viable cells from said antibodies.

2. The method of claim 1 in which the antibody is attached to an insoluble affinity matrix.

3. The method of claim 2 in which the matrix comprises immunomagnetic microspheres.

4. The method of claim 1 in which the antibody is a fluorescent-labeled antibody.

5. A method for the purification of lymphohematopoietic precursor cells comprising:

(a) treating a population of human cells containing CD34-positive cells with an affinity material comprising a monoclonal antibody specific for MY10 epitope;

(b) separating antibody-bound cells from unbound cells;

(c) treating the antibody-bound cells with chymopapain; and (d) separating non-cellular materials from the cells released by enzyme treatment.

* * * * *